Figure 1:
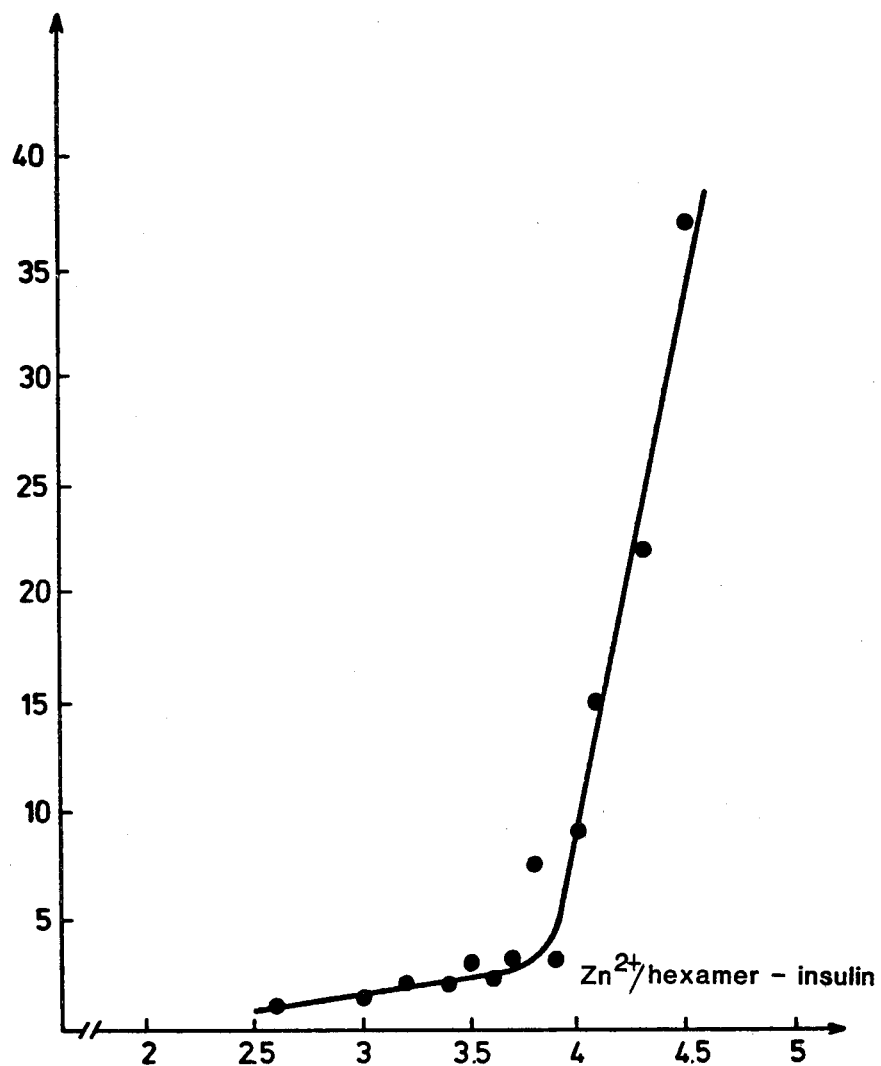

United States Patent [19]

Brange et al.

[11] Patent Number: 4,476,118

[45] Date of Patent: Oct. 9, 1984

[54] STABILIZED INSULIN PREPARATIONS

[75] Inventors: Jens J. V. Brange, Klampenborg; Svend Havelund, Hvidovre, both of Denmark

[73] Assignee: Novo Industri A/S, Denmark

[21] Appl. No.: 463,730

[22] Filed: Feb. 4, 1983

[30] Foreign Application Priority Data

Feb. 5, 1982 [DK] Denmark ............................ 491/82

[51] Int. Cl.³ .............................................. A61K 37/26
[52] U.S. Cl. ..................................................... 424/178
[58] Field of Search ......................................... 424/178

[56] References Cited

U.S. PATENT DOCUMENTS

| | | | |
|---|---|---|---|
| 2,787,575 | 4/1957 | Homan et al. | 424/178 |
| 2,882,202 | 4/1959 | Petersen et al. | 424/178 |
| 2,882,203 | 4/1959 | Petersen et al. | 424/178 |
| 3,014,842 | 12/1961 | Schlichtkrull | 424/178 |
| 3,058,885 | 10/1962 | Schlichtkrull | 424/178 |
| 3,091,573 | 5/1963 | Schlichtkrull | 424/178 |
| 3,584,121 | 6/1971 | Krayenbuhl et al. | 424/178 |

FOREIGN PATENT DOCUMENTS

1851/80  8/1980  Denmark .......................... 260/112.7

Primary Examiner—Frederick E. Waddell
Attorney, Agent, or Firm—Fidelman, Wolffe & Waldron

[57] ABSTRACT

Novel pharmaceutical solutions of dissolved insulin having improved physical stability prepared by incorporating therein an essentially ionized zinc salt in a concentration corresponding to a content of zinc ions at the disposal of the insulin of more than 4 $Zn^{2+}$/hexamer insulin preferably 4.2–4.5 $Zn^{2+}$/hexamer insulin. The solutions exhibit a stability factor exceeding 5.

The novel insulin solutions are particularly adapted for use in continuous insulin delivery equipment.

16 Claims, 2 Drawing Figures

100 IU PORCINE INSULIN per ml

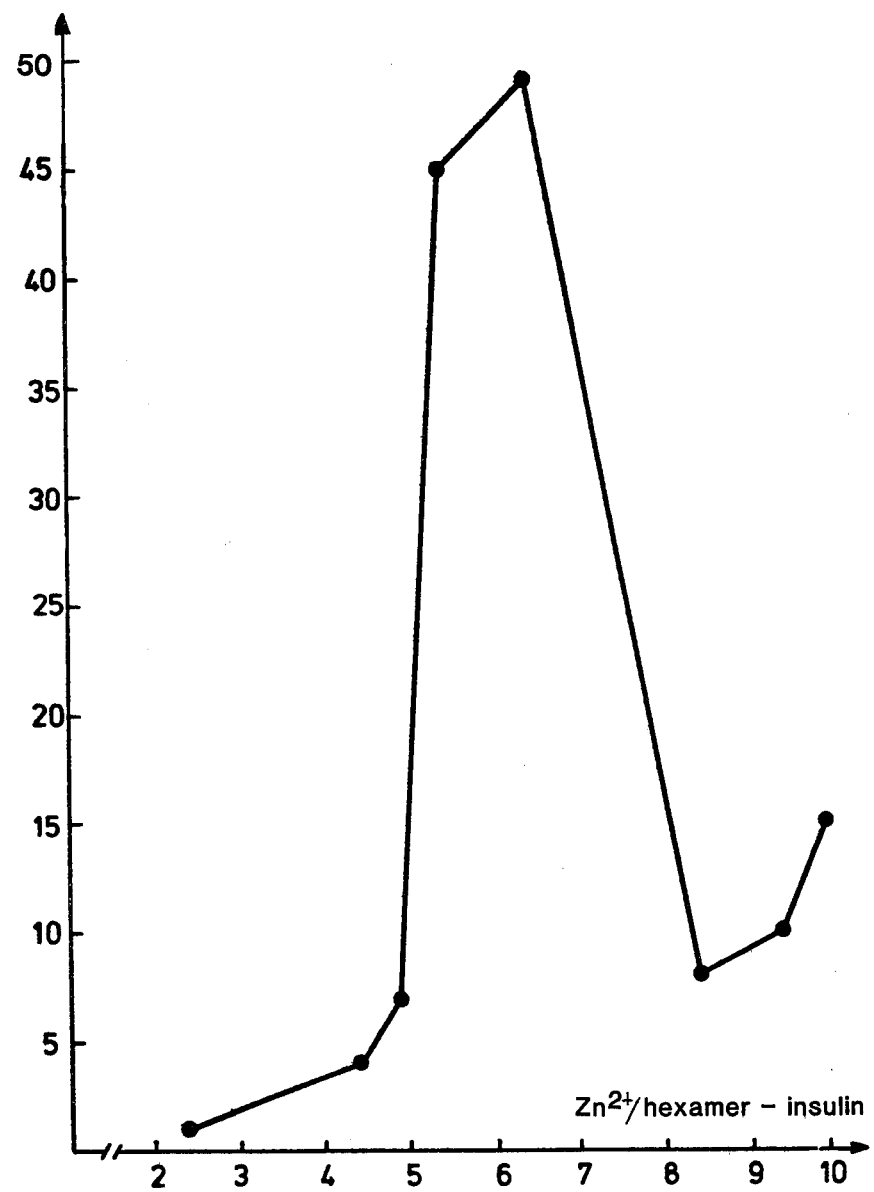

STABILIZED INSULIN PREPARATIONS

The present invention relates to novel stabilized insulin solutions which are specifically adapted for use in equipment for continuous insulin delivery, and to a process for producing such stabilized insulin solutions.

Over the past years steadily increasing efforts have been devoted to the development of portable or implantable systems for continuous infusion of insulin, the main aim of such efforts being to put at the disposal of the diabetic patient a regime of insulin administration which is more closely adaptable to diurnal variations in physiological insulin requirements than is possible by conventional insulin medication.

In essence, the mechanical part of a device for continuous insulin delivery comprises such elements as an insulin reservoir, a pumping system and a suitable catheter for delivering the insulin at the chosen site, which is usually located either subcutaneously, intravenously or in the peritoneal space. The pumping system may be automatically activated and may also be provided with an additional voluntary control for delivering insulin at times of specific needs.

If the insulin solution is supplied by a syringe this will also usually function as the insulin reservoir. Devices of the syringe type are generally carried extracorporeally. However, considerably more sophisticated systems have also been developed, in which the entire mechanical unit is constructed for implantation, usually subcutaneously. The insulin reservoir will usually be adapted for percutaneous refilling.

The propensity of insulin to precipitate out of commercially available solutions, thereby obstructing both mechanical parts and delivery catheters, has proved to constitute a major impediment to further development and clinical application of continuous infusion equipment. Furthermore, there are obvious reasons for endeavoring to decrease the size of any type of continuous delivery system, whereby a need is created for more concentrated insulin solutions than have been available heretofore, which again may further aggravate the above mentioned problems.

It is generally assumed that the explanation of the precipitation phenomenon has to be sought in the tendency of insulin to form insoluble fibrils, particularly when solutions thereof are kept at elevated temperatures for extended periods of time. There is also evidence to show that any type of motion of or in the solution, including, for example, the turbulence induced by its passage through a narrow lumen or orifice, induces insulin fibrillation. Evidently, insulin solutions are subjected to most or all of such actions in any type of continuous delivery equipment. The general shortcomings of prior art insulin preparations in this respect are amply documented in the literature, for example, in a recent review article by W. D. Lougheed et al. (Diabetologia Vol. 19 (1980) Pp. 1-9).

To solve this problem it has been proposed to use acid insulin solutions containing glutamic acid or aspartic acid, vide Diabetes 30, (1981), 83, or neutral insulin formulations containing a sugar, such as glucose (D. S. Schade et al.: Satelite-Symposium to 16th European Association for the Study of Diabetes-Meeting, Greece, Sept. 22-23, 1980, P. 107). Further, it has been proposed to use a non-ionic surfactant (H. Thurow: German Patent Application No. P2952119.5).

However, insulin is chemically unstable in acid, even below body temperature and may react, reversibly or irreversibly, with carbohydrates, vide J. Brange and S. Havelund, "Properties of Insulin in Solution,": Proceedings from International Symposium on Artificial Systems for Insulin Delivery Assisi Sept. 20-23, 1981, Raven Press (in press). Further, the above mentioned non-physiological surfactant could be regarded as undesirable in drugs for parenteral use.

Such inconveniences are overcome according to the present invention which provides novel insulin solutions in which the insulin is substantially less prone to precipitate under conditions prevailing in continuous insulin delivery equipment than has been the case with conventional insulin preparations.

The invention is based on the discovery that zinc ions at certain concentrations exert a highly stabilizing effect on neutral insulin solutions.

Zinc has been used for years as crystallization promoting metal for making insulin crystals. Insulin crystals used for the preparation of neutral insulin solutions, therefore, usually contain zinc, vide for instance Great Britain Pat. No. 840,870 and Denmark Pat. No. 116,527.

The art has recognized an upper limit for the zinc content in neutral insulin solutions of about one percent by weight of zinc ions (calculated on the basis of dry insulin crystals).

However, in the presence of substances forming slightly soluble or complex compounds with zinc, the preparations may contain considerably more zinc, provided the amount of zinc ions actually at the disposal of the insulin, i.e., not complexed by such substances, does not exceed the above mentioned upper limit. If the content of zinc ions at the disposal of the insulin exceeds the above mentioned upper limit of about one percent by weight corresponding to about 5 $Zn^{2+}$/hexamer insulin zinc-insulin complexes precipitate from the solution.

In order to be sure that precipitation of zinc-insulin complexes is avoided in the zinc content of commercial insulin preparations, the art has used zinc proportions well under the above upper limit and in fact, the applicants' investigation of all neutral commercial insulin preparations known to them has revealed that the zinc ions concentration therein is about 2-3.5 $Zn^{2+}$/hexamer insulin.

However, it has now been discovered that insulin preparations with a content of zinc ions of 2 and even up to 4 zinc atoms per hexamer insulin are unstable under conditions for continuous insulin delivery. Insulin precipitates in a few days.

It is, therefore, a surprising observation that an increase of the zinc ions content to concentrations in the range of 4-5, which is just below the limit of about 5 $Zn^{2+}$/hexamer insulin for Zn-insulin precipitation, actually exerts a stabilizing effect on insulin solutions under the above described conditions for continuous insulin delivery.

THE INVENTION

The present invention provides a zinc containing novel insulin solution suitable for use in continuous insulin delivery for being physically stable under conditions for such delivery and, optionally, containing also a preserving agent, an agent rendering the solution isotonic, and a pH-buffering agent, which solution is characterized by presence of an essentially ionized zinc salt in a concentration adequate to provide a content of zinc ions at the disposal of the insulin of more than 4 $Zn^{2+}$/hexamer insulin.

The expression "zinc ions at the disposal of the insulin" should be understood as relating to zinc ions not bound by other substances in a complex, for instance, citrate, glycine, or phosphate.

The upper limit for the zinc ion content is the amount of zinc which causes precipitation of the zinc insulin complex, i.e., about 5 $Zn^{2+}$/hexamer insulin as mentioned above.

In a preferred embodiment of the present invention, the content of zinc ions at the disposal of the insulin does not exceed 4.8 $Zn^{2+}$/hexamer insulin and preferably is in the range of from about 4.2 to about 4.5 $Zn^{2+}$/hexamer insulin.

Preferred zinc salts are zinc acetate and zinc chloride.

Another preferred embodiment of the invention involves the use of phenol as preserving agent and glycerol as an agent rendering the solution isotonic.

DISCUSSION OF THE INVENTION

As mentioned previously, the zinc proportions provided above refer to zinc ions at the disposal of the insulin. In the presence of zinc complexing agent some of the zinc is bound by the complexing agent. However, as the content of zinc ions at the disposal of the insulin should exceed 4 $Zn^{2+}$/hexamer insulin, the total zinc content in an insulin preparation that contains a zinc complexing agent will often be above the aforementioned limits to an extent depending upon the amount of and complexing constant of any zinc complexing agent(s) present.

It is often preferred to use a zinc complexing agent capable of increasing the operable range for total zinc content. Assuming, for instance, that some of the equipment used for reservoir, pumping system, tubings, etc. binds or releases zinc, the presence of a zinc complexing agent would ensure that the level of zinc ions at the disposal of the insulin is always inside the range for practice of the present invention.

Practice of this invention employs the narrow range for the proportions of zinc ions that substantially improve stability and inclusion of any particular complexing agent in the solution materially affects availability of zinc ions to the insulin, all of which indicates that considerable care is necessary to provide the between 4 and 5 $Zn^{2+}$/hexamer insulin at the disposal of the insulin. When no complexing agent will be present in the insulin solution, the quantity of $Zn^{2+}$ in an essentially ionized zinc salt at the disposal of the insulin can be predetermined readily by calculation. All is available. This is not true when a complexing agent is present in the solution. Calculations maybe unreliable. For insulin solution formulations that deviate from those preferred modes of the invention exemplified hereinafter, cut and try tests using, for example, the herein described stablty test, may be advisable to make certain that the contemplated complexing agents and their proportions do leave the preferred 4.2–4.5 $Zn^{2+}$/hexamer insulin at the disposal of the insulin. The total zinc content in the complexing agent containing insulin solution can be expected to be between 5 and 10 $Zn^{2+}$/hexamer insulin when weak complexing agents are present, and to be from about 10 to about 200 $Zn^{2+}$/hexamer insulin when strong complexing agents are present.

In addition to the stability test the upper limit for the total zinc content, e.g. the zinc content causing precipitation of the zinc insulin complex can be used to determine the amount of total zinc in the complexing agent containing insulin solution whereby a substantial increase in the stability may be achieved.

The inventors' experience has revealed that the total amount of zinc ions in the complexing agent containing insulin solution can be expected to be from about 50 to about 90% of the amount of zinc ions that would cause precipitation of the zinc insulin complex.

The total amount of zinc ions is preferably from about 60 to about 90% and more preferably from about 75 to about 90% of the amount of zinc ions that would cause precipitation of the zinc insulin complex.

The present invention, therefore, also provides a novel insulin solution suitable for use in continuous insulin delivery by being physically stable under conditions for such delivery and optionally comprising a preserving agent, an agent rendering the solution isotonic, and a pH-buffering agent and further comprising a zinc complexing agent, which solution is characterized in that the total zinc content is at least 5 $Zn^{2+}$/hexamer insulin and in preferred embodiments of the present invention the total zinc content is at least 6 $Zn^{2+}$/hexamer insulin.

The zinc complexing agents for use in the novel insulin solutions should be soluble and physiologically acceptable.

Suitable zinc complexing agents are amino acids, e.g., glycine, alanine, valine, leucine, isoleucine, serine threonine, phenyl alanine, proline, tryptophan, asparagine, glutamic acid, and histidine, and oligopeptides, such as diglycine.

Another group of suitable zinc complexing agents are carboxylic acids, such as acetic acid, or hydroxycarboxylic acids, such as citric acid, 3-hydroxybutyric acid, and lactic acid.

Preferred zinc complexing agents are glycine and citric acid. Also preferred are diglycine and histidine.

The minimum total zinc ion concentration for obtaining a substantial stabilizing effect, e.g., a stability factor as defined hereinafter in the range of 5–10, depends on which complexing agent is used. However, a stability factor of above 10 can be achieved and is preferred.

DETAILS OF THE INVENTION

The invention may now be explained in further detail with reference to the accompanying drawings in which:

FIG. 1 is a plot of the stability factor at 41° C. as a function of the zinc ion concentration (100 UI porcine insulin per ml prepared according to Example 1); and FIG. 2 is a plot of the stability factor at 41° C. as a function of the total zinc ions content in the presence of a weak complexing agent (40 IU porcine insulin per ml in 10 mM glycine prepared analogously with Example 7).

It may be seen from FIG. 1 how the stability of the insulin solution is drastically increased at a zinc ions content of above 4 $Zn^{2+}$/hexamer insulin.

In the presence of a weak complexing agent a substantial increase in the stability may be obtained at a nominally higher total zinc ion content, i.e., to what would calculate out to about 5 $Zn^{2+}$/hexamer insulin, because little of the zinc is bound by the complexing agent and accordingly is not at the disposal of the insulin.

As has been indicated above, measurement of stability can be employed to establish how much of the total zinc content in the insulin solution is at the disposal of the insulin. If desired, the stability factor defined hereinafter may be employed directly as a criterion for practice of this invention. The minimum stability factor for the zinc containing insulin solutions of the invention is 5; a stability factor exceeding 10 is preferred.

When a zinc complexing agent is present in the insulin solution, the upper limit for the total zinc content is the amount of zinc causing precipitation of the zinc insulin complex, a consequence that occurs when the content of zinc ions not bound by the complexing agent and therefore at the disposal of the insulin exceeds about 5 $Zn^{2+}$/hexamer insulin.

Neutral insulin preparations containing complexing agents or buffers forming complexes with zinc are known from the above mentioned Denmark Pat. No. 116,527 and Denmark Patent Application No. 1851/89. However, the highest described zinc content is 1% Zn calculated on the dry weight of insulin, vide the Examples 2 and 6 therein. The applicants have reproduced these two Examples, vide the following Examples 9 and 10 hereof. It appears therefrom that the known insulin preparations exhibit stability factors of only 3.5 and 1 respectively. Insofar as the inventors hereof are aware, the art has not heretofore provided the 4–5 $Zn^{2+}$/hexamer insulin at the disposal of the insulin which so substantially improves stability of the insulin solution.

LABORATORY RESULTS

With a preferred weak complexing agent, e.g., glycine 10 mM a significant stabilization is obtained at a total zinc content that calculates out to about 5 $Zn^{2+}$/hexamer insulin, vide the test results shown in Table I below and FIG. II; the preferred range for total zinc content is from about 5 to about 8 $Zn^{2+}$/hexamer insulin.

TABLE I

40 IU porcine insulin per ml in $10^{-2}$ molar solution of glycine with zinc concentration varied, prepared analogous to Example 7.

| Zinc Conc. (M) | $Zn^{2+}$/hexamer insulin* | Stability Factor |
|---|---|---|
| $1.0-10^{-4}$ | 2.4 | 1 |
| $1.8-10^{-4}$ | 4.4 | 4 |
| $2.0-10^{-4}$ | 4.9 | 7 |
| $2.2-10^{-4}$ | 5.4 | 45 |
| $2.6-10^{-4}$ | 6.4 | 49 |
| $3.4-10^{-4}$ | 8.4 | 8 |
| $3.8-10^{-4}$ | 9.4 | 10 |
| $4.0-10^{-4}$ | 9.9 | 15 |

*Total content of zinc ions

If a stronger zinc complexing agent is used, for instance, citric acid, a total zinc content of from about 40 to 200 $Zn^{2+}$/hexamer insulin is required to obtain significant stabilization, vide the test results shown in the following Table II.

TABLE II

40 IU porcine insulin per ml with zinc and citrate concentration varied, prepared analogous to Example 8.

| Zinc Conc. (M) | $Zn^{2+}$/hexamer insulin* | Citrate (M) | Stability Factor |
|---|---|---|---|
| $1.0-10^{-4}$ | 2 | $10^{-2}$ | 1 |
| $0.6-10^{-2}$ | 150 | $10^{-2}$ | 6 |
| $0.8-10^{-2}$ | 200 | $10^{-2}$ | 10 |
| $0.9-10^{-2}$ | 225 | $10^{-2}$ | 10 |
| $0.95-10^{-2}$ | 238 | $10^{-2}$ | 19 |
| $1.0-10^{-4}$ | 2 | $2.0-10^{-3}$ | 1 |
| $1.6-10^{-3}$ | 40 | $2.0-10^{-3}$ | 6 |
| $1.8-10^{-3}$ | 45 | $2.0-10^{-3}$ | 30 |
| $2.0-10^{-3}$ | 50 | $2.0-10^{-3}$ | 19 |

*Total content of zinc ions

The concentration of insulin in the solution is preferably in the range of 5 to 750 IU and more preferably from 40 to 500 IU per ml.

The present invention also comprises a method for preparing novel insulin solution suitable for use in continuous insulin delivery by being physically stable under conditions for such delivery and, optionally, comprising a preserving agent, an agent rendering the solution isotonic, and a pH-buffering agent, which method is characterized by incorporation into said insulin solution an essentially ionized zinc salt in a concentration corresponding to a content of zinc ions at the disposal of the insulin of more than 4 $Zn^{2+}$/hexamer insulin.

An exemplary mode of preparing the insulin solution of the present invention comprises dissolving crystalline zinc insulin, for example, a highly purified grade of insulin, such as "monocomponent" insulin (see Great Britain Pat. No. 1,285,023) in water in the presence of acid, for example, hydrochloric acid. An aqueous solution of the preserving agent, for example, phenol or an alkyl phenol, such as cresol, or methyl parahydroxybenzoate, is prepared separately, if desired also containing an osmotic pressure regulating agent, such as glycerol, preferably in an amount calculated to render the final solution isotonic and (if desired) a zinc complexing agent, such as citrate or glycine. This solution is then added to the acid insulin solution followed by addition of a base, for example, sodium hydroxide solution, to ajust the pH to neutrality. In this specification neutrality is to be understood as a pH value in the range of from about 7 to about 8. The calculated amounts of zinc salt, such as zinc acetate, buffering agent (if desired), such as TRIS, and zinc complexing agent may be added at this stage, followed by readjustment of pH. Alternatively, the zinc salt may be incorporated in the acid insulin solution prior to neutralization thereof. The resulting solution is finally filled up to the calculated volume with water, sterilized by filtration and subsequently transferred to sterile vials.

STABILITY TEST

The insulin solutions so prepared are subjected to a stability test under forced conditions in the following manner:

Vials (of 12.5 ml capacity) containing the test sample (10 ml) and each provided with a rubber cap are placed vertically on a shaking platform (Type 01 T623TBSH02, supplied by HETO, Birkerød, Denmark) which is totally immersed in a water bath kept at 41° C.±0.1° C. The platform is subjected to horizontal rocking movements with a frequency and amplitude of 100 rpm and 50 mm, respectively.

The opalescence of the test samples is monitored at regular time intervals on a Fischer DRT 1000 nephelometer provided with an adapter for vials. Fibrillation time is defined as the lapse of time until the test sample develops a turbidity of 10 nephelometric turbidity units (NTU).

Each test is conducted with test samples and control samples without added zinc salt (4–5 vials of each) treated side by side. The control samples correspond to the test samples apart from containing about 2 $Zn^{2+}$/hexamer, the zinc in the control samples originating from the crystallization of the insulin (the samples were in fact, taken from commercially available insulin solutions, and the control results correspond then to stability characteristics heretofore prevalent in widely used insulin solutions).

The stability factor is calculated as the ratio of the average fibrillation time of the test samples to that of the control samples Further details of practising the present invention are furnished by way of the following Examples which, however, should not be construed so as to impose any kind of limitation of the scope of the invention.

In the Examples, aqueous solution and water were sterilized, the former by filtration, and subsequent operations thereof were conducted under aseptic conditions.

EXAMPLE 1

100 I.U. porcine insulin per ml containing 4.2 $Zn^{2+}$/hexamer insulin

Crystalline monocomponent porcine insulin (264 mg) containing 0.4 percent of zinc and having a total activity of 10,000 I.U. was dissolved in water (50 ml) containing hydrochloric acid (325 $\mu$l of N) followed by the addition of an aqueous solution (25 ml) containing glycerol (1.6 g) and phenol (200 mg). The pH of the solution was adjusted to 7.5 by means of sodium hydroxide solution. Zincacetate (1.56 ml of 10 mM solution) was added and pH readjusted to 7.5 and the total volume to 100 ml with water. The resulting solution was sterilized by filtration and subsequently transferred aseptically to vials (10 ml).

Stability factor: >15.

EXAMPLE 2

500 I.U. porcine insulin per ml containing 4.2 $Zn^{2+}$/hexamer insulin

Crystalline monocomponent porcine insulin (20.75 g) containing 0.4% of zinc and having a total activity of 550,000 I.U. was dissolved in water (550 ml) containing hydrochloric acid (10 ml of N).

To an aliquot of this solution (50 ml) was added zinc acetate (72 $\mu$l of M solution) followed by the addition of an aqueous solution (25 ml) containing glycerol (1.6 g) and phenol (200 mg). The pH of the solution was adjusted to 7.4 by means of sodium hydroxide solution and the total volume to 100 ml with water. The resulting solution was sterilized by filtration and subsequently transferred aseptically to vials (10 ml).

Stability factor: 5.

EXAMPLE 3

100 I.U. human insulin per ml containing 4.3 $Zn^{2+}$/hexamer insulin

Crystalline monocomponent human insulin (1.67 g) containing 0.4% of zinc and having a total activity of 45,000 I.U. was dissolved in water (225 ml) containing hydrochloric acid (1.46 ml of N). To an aliquot of this solution (25 ml) was added zinc acetate (100 $\mu$l of 0.1 M solution) followed by the addition of an aqueous solution (10 ml) containing glycerol (0.8 g) and phenol (0.1 g). The pH of the solution was adjusted to 7.4 by means of sodium hydroxide solution and the volume to 50 ml with water. The resulting solution was sterilized by filtration and subsequently transferred aseptically to vials (10 ml).

Stability factor: 26.

EXAMPLE 4

100 I.U. porcine insulin per ml containing 4.5 $Zn^{2+}$/hexamer insulin

The procedure was analogous to that of example 1 except that 1.89 ml of 10 mM zinc acetate solution was added thus affording an amount of 4.5 $Zn^{2+}$ per hexamer insulin.

Stability factor: >33

EXAMPLE 5

40 I.U. human insulin per ml containing 4.2 $Zn^{2+}$/hexamer insulin

Crystalline monocomponent human insulin (741 mg) containing 0.4% zinc and having a total activity of 20,000 IU was dissolved in water (60 ml) containing hydrochloric acid (640 $\mu$l of N) and zinc acetate (3.96 ml of 0.01 M). An aqueous solution (400 ml) of phenol (1 g) and glycerol (8 g) was added and finally the pH adjusted to 7.45 by sodium hydroxide solution and the volume made up to 500 ml with water. The solution was sterilized by filtration and subsequently transferred aseptically to vials (10 ml).

Stability factor: 34

EXAMPLE 6

100 I.U. human insulin per ml containing 4.2 $Zn^{2+}$/hexamer insulin in $10^{-2}$ molar of TRIS Crystalline monocomponent human insulin (1852 mg) containing 0.4% zinc and having a total activity of 50,000 IU was dissolved in water (60 ml) containing hydrochloric acid (1600 $\mu$l of N) and zinc acetate (99 $\mu$l of M). An aqueous solution (400 ml) of phenol (1 g) and glycerol (8 g) was added and finally the pH adjusted to 7.45 by TRIS (606 mg) and sodium hydroxide solution and the volume made up to 500 ml with water. The resulting solution was sterilized by filtration and subsequently transferred aseptically to vials (10 ml).

Stability factor: 16

EXAMPLE 7

40 I.U. porcine insulin per ml in $2.6 \cdot 10^{-4}$ and $10^{-2}$ molar solution of zinc and glycine, respectively Crystalline monocomponent porcine insulin (1.49 g) containing 0.4% zinc and having a total activity of 40,000 IU was dissolved in water (120 ml) containing hydrochloric acid (1280 $\mu$l of N) followed by addition of an aqueous solution (730 ml) of phenol (2 g), glycerol (8 g) and glycine (751 mg). The pH was adjusted to 7.5 by means of sodium hydroxide solution. Zinc acetate (160 $\mu$l of M) was added, pH readjusted to 7.5 and the volume made up to a total of 1000 ml with water. The solution was sterilized by filtration and subsequently transferred aseptically to vials (10 ml).

Stability factor: 63

EXAMPLE 8

40 I.U. porcine insulin per ml in $1.8 \cdot 10^{-3}$ and $2 \cdot 10^{-3}$ molar solution of zinc and citrate respectively Crystalline monocomponent porcine insulin (746 mg) containing 0.4% zinc and having a total activity of 20,000 IU was dissolved in water (60 ml) containing hydrochloric acid (640 $\mu$l of N). An aqueous solution (400 ml) of phenol (1 g) and glycerol (8 g) was added and the pH adjusted to 7.5 by sodium hydroxide solution. Citric acid (210 mg of monohydrate) and zinc acetate (850 $\mu$l of M) was added and pH readjusted to 7.5. The solution was sterilized by filtration and subsequently transferred aseptically to vials (10 ml).

Stability factor: 30

EXAMPLE 9 (comparison)

40 I.U. bovine insulin per ml in 13.3 mM solution of sodium phosphate. (Total zinc 1% ~ about 5.5 $Zn^{2+}$/hexamer insulin.)

Example 2 of Danish Pat. No. 116 527 was reproduced. The zinc content was adjusted to about 5.5 $Zn^{2+}$/hexamer insulin by addition of zinc acetate and pH was readjusted to 6.91. The solution was sterilized by filtration and subsequently transferred aseptically to vials (10 ml).

Stability factor: 3.5

EXAMPLE 10 (comparison)

40 I.U. bovine insulin per ml in 10 mM solution of citrate. (Total zinc 1% ~ about 5.5 $Zn^{2+}$/hexamer insulin)

Example 6 of Danish Pat. No. 116 527 was reproduced. The zinc content was adjusted to about 5.5 $Zn^{2+}$/hexamer insulin by addition of zinc acetate and pH was readjusted to 7.5. The solution was sterilized by filtration and subsequently transferred aseptically to vials (10 ml).

Stability factor: 1

In the claims:

1. An insulin solution suitable for use in continuous insulin delivery characterized by being physically stable under conditions for such delivery optionally, comprising a preserving agent, an agent rendering the solution isotonic, and a pH-buffering agent, which solution contains essentially ionized zinc in a concentration corresponding to a content of zinc ions at the disposal of the insulin of more than 4 $Zn^{2+}$/hexamer insulin but below the limit for Zn insulin precipitation.

2. The insulin solution according to claim 1, containing zinc ions at the disposal of the insulin in proportions less than about 4.8 $Zn^{2+}$/hexamer insulin.

3. The insulin solution according to claim 1 wherein the content of zinc ions at the disposal of the insulin in said solution is in the range of from about 4.2 to about 4.5 $Zn^{2+}$/hexamer insulin.

4. The insulin solution according to claim 1 wherein the zinc salt is zinc acetate or zinc chloride.

5. The insulin solution according to claim 1 wherein the preserving agent contains phenol and the agent rendering the solution isotonic contains glycerol.

6. The insulin solution according to claim 1 wherein the pH is in the range of about 7 to 8.

7. The insulin solution according to claim 1 wherein the the insulin concentration is in the range of 40 to 500 international insulin units per ml.

8. The insulin solution according to claim 1 further comprising a complexing agent, and wherein the total zinc content would calculate out to be at least 5 $Zn^{2+}$/hexamer insulin provided that the content of zinc ions at the disposal of the insulin is at least more than 4 $Zn^{2+}$/hexamer of insulin as foresaid.

9. The insulin solution according to claim 8 wherein the total zinc content would calculate out to be at least 6 $Zn^{2+}$/hexamer insulin.

10. The insulin solution according to claim 8 wherein the zinc complexing agent comprises glycine or citric acid.

11. The insulin solution according to claim 1 wherein a weak complexing agent is present, and wherein the total zinc content would calculate out to be in the range of from about 5 to about 8 $Zn^{2+}$/hexamer insulin provided that the content of zinc ions at the disposal of the insulin is at least more than 4 $Zn^{2+}$/hexamer of insulin as foresaid.

12. The insulin solution according to claim 1 further characterized by a stability factor exceeding 5.

13. The insulin solution according to claim 8 wherein the amount of zinc ions present is from about 50 to about 90% of the amount of zinc ions that would cause precipitation of zinc insulin complex.

14. The insulin solution according to claim 13 wherein the amount of zinc ions present is from about 60 to about 90% of the amount of zinc ions that would cause precipitation of zinc insulin complex.

15. The insulin solution according to claim 13 wherein the amount of zinc ions present is from about 75 to about 90% of the amount of zinc ions that would cause precipitation of zinc insulin complex.

16. A method for producing an insulin solution suitable for use in continuous insulin delivery for being physically stable under delivery conditions, optionally, comprising a preserving agent, an agent rendering the solution isotonic, and a pH buffering agent, which method comprises incorporating into said insulin solution an essentially ionized zinc salt in concentration corresponding to a content of zinc ions at the disposal of the insulin of between 4 and 5 $Zn^{2+}$/hexamer insulin.

* * * * *